(12) United States Patent
Kojima et al.

(10) Patent No.: US 7,419,727 B2
(45) Date of Patent: Sep. 2, 2008

(54) ORGANIC ELECTROLUMINESCENT DEVICE

(75) Inventors: Kazushige Kojima, Aichi (JP); Kojiro Tachi, Aichi (JP); Hisayoshi Fujikawa, Aichi (JP); Koji Noda, Aichi (JP); Masahiko Ishii, Aichi (JP); Yasunori Taga, Aichi (JP); Makoto Satsuki, Okayama (JP); Makoto Fujiwara, Okayama (JP); Natsuko Ishida, Okayama (JP); Sadaharu Suga, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 118 days.

(21) Appl. No.: 10/545,165

(22) PCT Filed: Feb. 12, 2004

(86) PCT No.: PCT/JP2004/001447

§ 371 (c)(1), (2), (4) Date: Aug. 11, 2005

(87) PCT Pub. No.: WO2004/072206

PCT Pub. Date: Aug. 26, 2004

(65) Prior Publication Data

US 2006/0192473 A1 Aug. 31, 2006

(30) Foreign Application Priority Data

Feb. 12, 2003 (JP) ............................. 2003-033712

(51) Int. Cl.
*H01L 51/50* (2006.01)

(52) U.S. Cl. ...................... 428/690; 428/917; 313/504; 313/506

(58) Field of Classification Search ................ 428/690, 428/917; 313/504, 506, 483
See application file for complete search history.

(56) References Cited

U.S. PATENT DOCUMENTS 5,635,308 A * 6/1997 Inoue et al. ................. 428/696

(Continued)

FOREIGN PATENT DOCUMENTS

JP 11-354280 12/1999

(Continued)

OTHER PUBLICATIONS

Van Slyke et al., Appl. Phys. Lett., vol. 69 (15), Oct. 7, 1996, p. 2160-2162.*

(Continued)

*Primary Examiner*—Dawn Garrett
(74) *Attorney, Agent, or Firm*—Browdy and Neimark

(57) ABSTRACT

This invention has an objective to improve durability at elevated temperature in organic electroluminescent devices using coumarin derivatives as dopant in a luminescent layer. This invention attains the above objective by providing in the organic electroluminescent devices formed by laminating an anode, a hole injection layer, a hole transportation layer, a luminescent layer, an electron transportation layer and a cathode in this order, the luminescent layer which comprises as dopant the green light-emitting coumarin derivative and hole- and electron-transporting substances as host; said coumarin derivative consisting of a plurality of coumarin groups bound to an aromatic ring, heterocycle, or any combination thereof, and exhibiting a glass transition point of 150° C. or higher or a melting point of 297° C. or higher.

4 Claims, 2 Drawing Sheets

U.S. PATENT DOCUMENTS

| | | | |
|---|---|---|---|
| 6,020,078 A * | 2/2000 | Chen et al. | 428/690 |
| 6,285,039 B1 * | 9/2001 | Kobori et al. | 257/40 |
| 2004/0124766 A1 * | 7/2004 | Nakagawa et al. | 313/504 |
| 2005/0089713 A1 * | 4/2005 | Satsuki et al. | 428/690 |
| 2005/0275341 A1 * | 12/2005 | Satsuki et al. | 313/504 |

FOREIGN PATENT DOCUMENTS

| | | |
|---|---|---|
| JP | 2000-182772 | 6/2000 |
| JP | 2000-192028 | 7/2000 |
| JP | A 76876/01 | 3/2001 |
| JP | 2001-329257 | 11/2001 |
| JP | A 226484/02 | 8/2002 |

OTHER PUBLICATIONS

Fujiwara, M. et al., "Investigation of Blue Dopant Used Coumarin Derivatives," Journal of Photopolymer Science and Technology, vol. 15, No. 2(2002)237-238.

* cited by examiner

US 7,419,727 B2

ORGANIC ELECTROLUMINESCENT DEVICE

TECHNICAL FIELD

The present invention relates to an organic electroluminescent device (abbreviated as "organic EL device" hereinafter) where a coumarin derivative is used as dopant in the luminescent layer of the organic EL device.

BACKGROUND ART

In this age of the growing importance of information, organic EL devices have been highlighted as displaying device of the next generation. Hitherto, cathode-ray tubes have been predominantly used in information displaying equipments in larger sizes. Cathode-ray tubes are however large in both volume and weight and high in operation voltage, thus they may be unsuitable in compact equipments.

More required are information displaying equipments which are in a thinner and lighter panel form and operable with a lower voltage and less power consumption. Liquid crystal devices have been extensively used in various fields because of the merit that they are operable with a lower voltage and less power consumption.

Liquid crystal devices however have the demerits that one can hardly receive a clear information therefrom when he or she views them at an angle outside the specific ranges, as well as that their power consumption is not so low as expected because they usually require backlight. Organic EL devices have been proposed as information displaying means which may overcome the above demerits.

Organic EL devices are classified into light-emitting devices which utilize a luminescence such as fluorescence or phosphorescence: They usually comprise a luminescent layer incorporated with a luminescent compound and inserted between a cathode and anode to which dc voltage is energized to inject holes and electrons in the luminescent layer so that a pair of hole and electron recouple each other to make in the luminescent compound an excited state which subsequently returns to the ground state to emit such a luminescence.

Organic EL devices are characterized in that their luminescent color tint can be controlled to a desired level by selecting an appropriate organic compound to be used as host compound in forming a luminescent layer, and screening a guest compound (or dopant) which may most suit to the host compound. Further, luminescence brightness and life expectancy may be remarkably improved, depending upon the combination of host-and guest-compounds.

Organic EL devices have been deemed to be excellent in principle because of the fact that they emit light in an autonomous manner, and this removes the dependency of visual field angle from information displaying equipments. Also, that they require no backlight and this would advantageously save power consumption.

Many of organic EL devices proposed hitherto however have a problem of durability: Their brightness may decay within a short period of time when used under severe conditions, for example, in case of equipping them to cars and automobiles where mechanical vibrations and high temperatures are unavoidable.

In display panels which are driven in dot matrix mode and required for elevated brightness, any brightness decay would be a serious problem. Such decay is most remarkable in green light-emitting devices which usually exhibit the highest brightness in full color panels. This may be due to the fact that there have been available no green dopant materials with a high efficiency and satisfactorily high thermal resistance.

As to green dopant materials, coumarin derivatives have been employed in usual cases. They may be useful as functional organic materials in the field of organic electronics, particularly, as luminescent materials in organic EL devices because they have absorption and luminescent maxima in the visible region, as well as having a property of emitting a visible light when excited.

3-(2-benzothiazolyl)-7-(diethylamino) coumarin, a typical high efficient green dopant material commercialized under the trade name of "COUMARIN 6" for use in conventional organic EL devices, has been proved to be insufficient for durability at elevated temperature because its glass transition point is not so high (99° C.). Because of this, it is hard to apply it to organic EL devices directed to use in cars and automobiles which causes elevated temperature, for example, 100° C. or higher.

In order to realize an enhanced durability which may render coumarin derivatives useful as dopant in organic EL devices, there have been proposed a series of coumarin derivatives which bear at the C-3 position in coumarin skeleton a benzothiazolyl group as substituent and form a julolidine ring including carbons at the C-6 to C-8 positions in coumarin skeleton, in addition to another series of coumarin derivatives where a hydrocarbon group is bound to the C-4 position in coumarin skeleton and a julolidine- and a benzothiazole-groups are placed at any positions other than the C-4 position in coumarin skeleton: Such a coumarin derivative may exhibit an enhanced durability at elevated temperature while retaining the high efficient green luminescence of COUMARIN 6 (see Japanese Patent Kokai Nos. 2001-76,876 and 2002-226,484).

Although coumarin derivatives as disclosed in Japanese Patent Kokai Nos. 2001-76,876 and 2002-226,484 have been proved to be capable of emitting a remarkable luminescence in the green region and this may render them very useful as luminescent agent in organic EL devices, as well as of much more enhancing durability at elevated temperature than COUMARIN 6, the improvement is not enough to apply them to organic EL devices directed to use in cars and automobiles where ambient temperature for organic EL devices becomes 100° C. or higher because the glass transition point of such a coumarin derivative is still 150° C. or lower.

In view of the above described problems, the objective of the present invention is to improve the durability at elevated temperature in organic EL devices where coumarin derivatives are used as dopant in luminescent layer.

DISCLOSURE OF INVENTION

To attain the above objective, an aspect of the present invention is characterized in that in an organic EL device which comprises an anode (20), a hole transportation layer (40), a luminescent layer (50), an electron transportation layer and a cathode (70), the luminescent layer (50) comprises a green light-emitting coumarin derivative as dopant and hole- and electron-transporting substances as host; said coumarin derivative comprising a plurality of coumarin groups bound to an aromatic ring, heterocycle or any combination thereof, and exhibiting either a glass transition point of 150° C. or higher or a melting point of 297° C. or higher.

According to this aspect, the molecular weight of coumarin derivative is increased to at least 2-folds larger than those of conventional coumarin derivatives by allowing a plurality of coumarin groups to bind to an aromatic ring, heterocycle or any combination thereof, resulting in a remarkable enhancement in heat resistance. Thus, such coumarin derivative eventually exhibits a glass transition point of 150° C. or higher or a melting point of 297° C. or higher.

Further, the durability at elevated temperature in organic EL devices can be enhanced by using such coumarin derivative with an elevated thermal resistance as a dopant in luminescent layer. Still further, durability at elevated temperature can be much more improved by using as host in a luminescent layer the mixture of a material which functions as a hole transportation layer, and another material which functions as an electron transportation layer.

When such materials are used as host, a hole transporting substance predominantly transports holes in luminescent layer, while an electron transporting substance predominantly transports electrons. Because of this, any simultaneous injection of holes and electrons into hole- and electron-transporting substances in host materials is effectively suppressed to reduce any luminescence from host, resulting in the enhancement of durability in host.

Since in this way, the present invention attains a luminescent layer comprising as dopant a coumarin derivative which is higher in thermal resistance than conventional coumarin derivatives and a host material with an elevated durability, the organic EL device according to the present invention much more improves durability at elevated temperature than conventional organic EL devices.

Further, the organic EL device according to the present invention using such coumarin derivative emits a visible light in the green region and the emission consistently prolongs over a long period of time even when the organic EL device is driven under elevated temperature conditions.

As to the coumarin derivative, one can employ those which consist of at least one of the compounds represented by the following Chemical Formulae 4 to 6.

Chemical Formula 4:

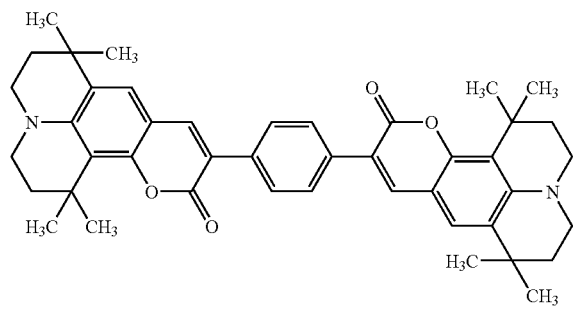

Chemical Formula 5:

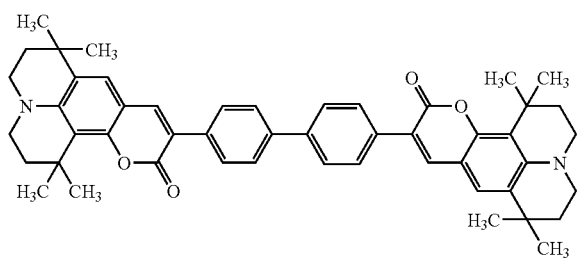

Chemical Formula 6:

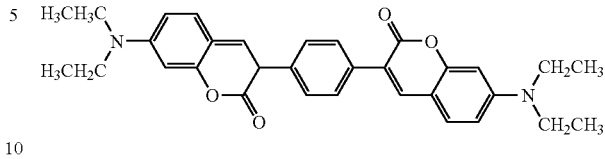

Another aspect of the present invention described in claim 3 on file is characterized in that a hole transporting substance in the luminescent layer (50) is the same as that in the hole transportation layer (40).

Since according to this aspect, the hole transporting substance in the luminescent layer is the same as that in the hole transportation layer, the injection of holes from the hole transportation layer into the luminescent layer is facilitated to enhance the efficiency, and the use of the same substance with different purposes would reduce.

Still another aspect of the present invention is characterized in that an electron transporting substance in the luminescent layer (50) is the same as that in the electron transportation layer (60).

Since according to this aspect, the electron transporting substance in the luminescent layer is the same as that in the electron transportation layer, the injection of electrons from the electron transportation layer into the luminescent layer is facilitated to enhance the efficiency, and the use of the same substance with different purposes would reduce.

Still another aspect of the present invention is characterized in that a hole transporting substance in the luminescent layer (50) is the same as that in the hole transportation layer (40), as well as that an electron transporting substance in the luminescent layer (50) is the same as that in the electron transportation layer (60).

According to this aspect, one can obtain effects similar to those attained in accordance with the hole transporting substance is the same as the hole transportation layer, or the electron transporting substance in the luminescent layer is the same as that in the electron transportation layer.

Still another aspect of the present invention is characterized in that the ratio of a hole transporting substance against host in the luminescent layer (50) is 1 to 10% by mass. Still another aspect of the present invention on file is characterized in that the ratio of an electron transporting substance against host in the luminescent layer (50) is 99 to 90% by mass.

The aspects of the present invention wherein the ratio of th hole transport ing substance to the host in the luminescent layer is 1 to 10% by mass, or that the ratio of the electron transporting substance to the host in the luminescent layer is 9 to 90% by mass are to specify the ratio of hole- and electron-transporting substances against host in luminescent layer. According to these aspects, the balance between holes with a higher mobility and electrons with a lower mobility in the luminescent layer (50) is kept in a prescribed level to enhance both efficiency and durability.

Still another aspect of the present invention on file is characterized in that the glass transition temperatures of hole- and electron-transporting substances in the luminescent layer (50) are 120° C. or higher.

According to this aspect, the glass transition temperatures of hole- and electron-transporting substances in the luminescent layer (50) are 120° C. or higher and this is favorable to enhance durability at elevated temperature.

By the way, in case that a hole injection layer is provided between anode and hole transportation layer, it is preferable to use a hole injection layer consisting of copper phthalocyanine (abbreviated as "CuPc", hereinafter). This is due to the fact that CuPc is large in intramolecular polarization and this enhances adhesiveness to the anode (20).

To enhance stability at elevated temperature, it is important to increase interfacial adhesiveness to the anode (20). It is preferred to provide as hole injection layer on the anode (20) a layer of porphyrin compound which undergoes less crystallographic changes.

The present inventors studied changes in crystalline state of CuPc membrane when CuPc, a type of porphyrin compound, is used in hole injection layer which comes into contact with anode.

As a result, the present inventors found that the crystalline state of CuPc membrane considerably changes during standing under elevated temperature conditions. The following illustrates the result of studies on changes in crystalline states of CuPc membrane.

To quickly confirm changes in crystalline states, the standing temperature was set to a higher level (120° C.) for acceleration and evaluation was carried out upon 2-hour standing. Standing under such conditions will be designated as "accelerating high temperature standing" hereinafter.

On a glass substrate was formed an anode consisting of ITO (indium-tin oxide), and the surface of the anode was then subjected to a treatment using argon/oxygen plasma, after which CuPc membrane was formed on the anode. FIG. 2 shows the result of x-ray diffraction analysis on crystalline state of CuPc membrane carried out before and after accelerating high temperature standing.

As shown in FIG. 2, in the diffraction diagram, a peak appearing at $2\theta=6.68°$ reflects the crystal structure of CuPc. In FIG. 2, the full line curve shows a peak (initial peak) which appeared at $2\theta=6.68°$ before accelerating high temperature standing, while the dashed line curve shows a peak which appeared at $2\theta=6.68°$ after accelerating high temperature standing (2-hour standing at 120° C.).

A larger integration value or larger height in prescribed peak shows a higher crystallinity in CuPc membrane. In FIG. 2, the peak increased to 1.5-folds of that before accelerating high temperature standing in terms of integration value.

Because of this, the present inventors concluded that such change in crystalline state of CuPc membrane arose after providing an amorphous hole injection layer, a hole transportation layer, a luminescent layer, an electron transportation layer and a cathode on CuPc membrane as crystalline hole injection layer (or after finishing a luminescent device form), as well as that this was causative of reducing adhesiveness of CuPc membrane.

The present inventors further concluded that the adhesiveness of the CuPc membrane, particularly, its interfacial adhesiveness to the anode can be enhanced by forming CuPc membrane in such a manner that its crystallinity increases as much as possible.

As seen from the aspect of the present invention, further studies revealed that in the case of providing between the anode (20) and hole transportation layer (40) the hole injection layer (30) which consists of CuPc, the variation of diffraction peak by heating at an ambient temperature for organic EL device is to fall within ±25% of diffraction peak before heating, in terms of value for diffraction peaks as determined by applying x-ray diffraction method to CuPc.

Thus, the adhesiveness of CuPc membrane can be enhanced by minimizing changes in crystalline state of CuPc membrane as hole injection layer under elevated temperature conditions. In consequence, this is favorable to enhance durability at elevated temperature. Further, any irregularity on CuPc membrane caused by temperature variation is minimized, suppressing short-circuit or electric leakage.

The above parenthesized reference numerals for particular elements or means are to correspondingly refer to the same elements or means in the embodiments as described heretofore.

EXPLANATION OF SYMBOLS

20: Anode
30: Hole injection layer
40: Hole transportation layer
50: Luminescent layer
60: Electron transportation layer
70: Cathode

PREFERRED EMBODIMENT FOR CARRYING OUT THE INVENTION

The organic EL device in this embodiment bears an anode, a hole transportation layer, a luminescent layer, an electron transportation layer and a cathode: A hole injection layer is provided between the anode and hole transportation layer, while an electron injection layer, between the electron transportation layer and cathode, if necessary.

The luminescent layer comprises a green light-emitting coumarin derivative as dopant and hole- and electron-transporting substances as host; said coumarin derivative comprising a plurality of coumarin moieties bound to an aromatic ring, heterocycle, or any combination thereof, and exhibiting either a glass transition point of 150° C. or higher or a melting point of 297° C. or higher.

As well known in the art, the basic operation of such an organic EL device essentially consists of the steps of injecting electrons and holes from electrodes, allowing the electrons and holes to move into solids, allowing the electrons and holes to recouple each other to give singlet or triplet excitons, and allowing the excitons to emit a light.

Since the coumarin derivatives in this embodiment consistently prolong its emission over a long period of time, one can obtain an organic EL device having an extremely long life expectancy, provided that any emission from host is suppressed. As to the host, to suppress any emission therefrom, it is very effective to use as host a mixture layer consisting of hole- and electron transporting substances.

Figure 1:
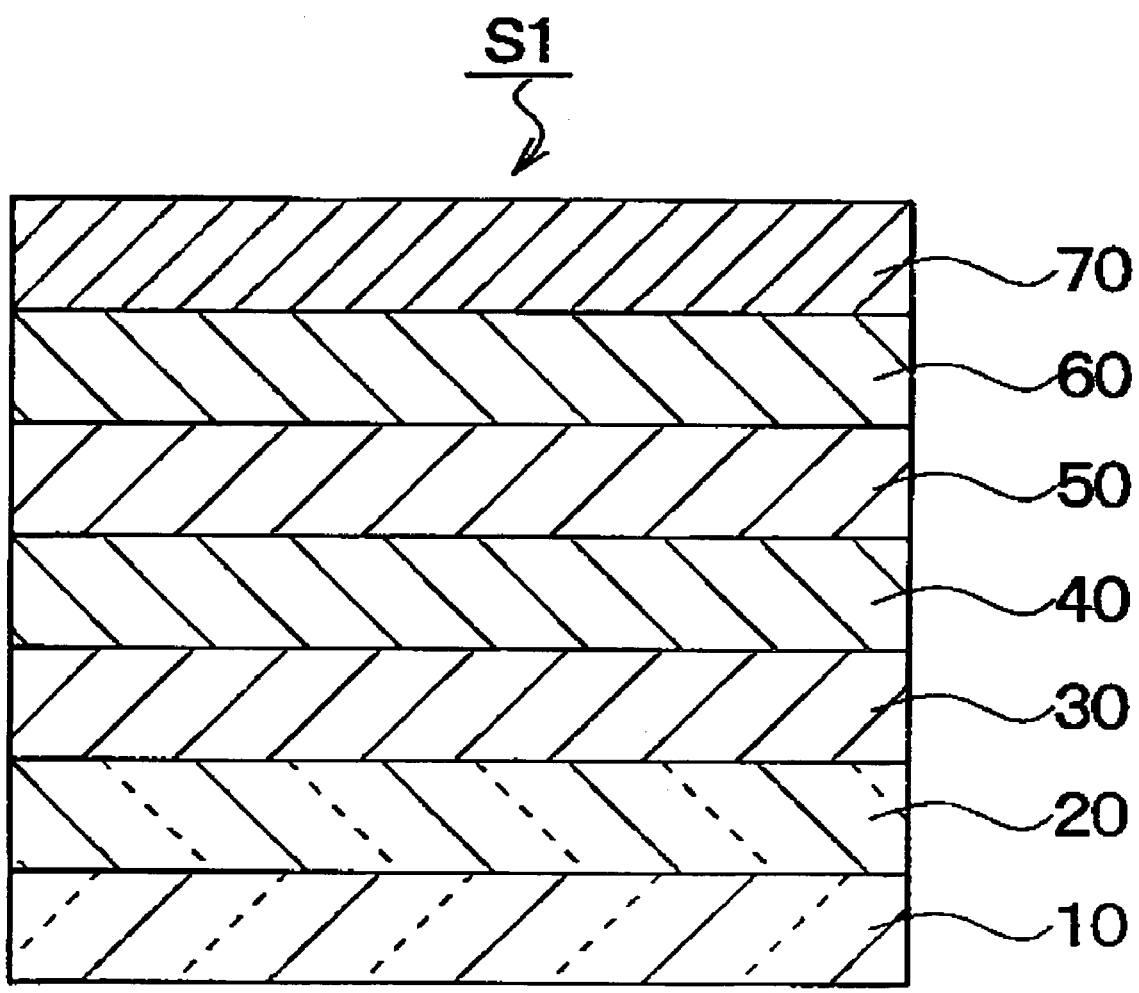
FIG. 1 is to illustrate the sectional structure in an embodiment for organic EL device according to the present invention.

The organic EL devices in this embodiment will be further explained. FIG. 1 is to illustrate the sectional structure in an embodiment for organic EL device according to the present invention.

In FIG. 1, the reference numeral 10 represents a substrate which is usually provided by forming a conventional substrate material including a glass such as soda glass, barium silicate glass, or aluminosilicate glass; a plastic such as polyester, polycarbonate, polysulfone, poly(methyl methacrylate), polypropylene, or polyethylene; or a ceramic such as quartz, or earthenware into a plate, sheet or film; which may be laminated each other, if necessary.

Preferred substrate materials are transparent glasses and plastics, while opaque ceramic materials such as silicon may be used in combination with a transparent electrode material(s). When it is necessary to control the chromaticity of luminescence, a chromaticity adjusting means such as a filter membrane, chromaticity conversion membrane, and dielectric reflection membrane are provided in an appropriate part of the substrate 1.

The reference numeral 20 represents an anode formed by allowing one or more metals or electric conductive compounds, which are low in electric resistivity but high in optical transmissivity throughout the visible region, to contact with either surface of the substrate 10 by using a method such as vacuum deposition, spattering, chemical vapor deposition (CVD), atom layer epitaxy (ALE), embrocation or immersion.

The anode 20 is formed by preparing the above compounds into a single or plurality of membranes with a thickness of 10 to 1,000 nm, desirably, 50 to 500 nm to give an electric resistivity of 1 kΩ/□ or lower, desirably, 5 to 50Ω/□ for the anode 20.

Examples of the electric conductive materials feasible in the anode 20 are metals such as gold, platinum, silver, copper, cobalt, nickel, palladium, vanadium, tungsten, and aluminium; metal oxides such as zinc oxide, tin oxide, indium oxide, and mixtures of tin oxide and indium oxide (abbreviated as "ITO" hereinafter); and electric conductive oligomers and polymers composed of repeating units of aniline, thiophene, or pyrrole.

Among these, ITO is characterized in that one can easily obtain preparations with a reduced resistivity, as well as in that minute patterns can be easily provided by etching with acids.

The reference numeral 30 represents a hole injection layer, which is usually formed with the method similarly as used in the anode 20 by preparing a hole injection material into a membrane with a thickness of 1 to 100 nm while allowing it to contact with the anode 20.

As to the hole injection materials, it is desirable to choose materials which exhibit a low ionization potential and a hole mobility of, for example, at least $10^{-6}$ cm$^2$/V·second under an electric field of $10^4$ to $10^6$ V/cm so as to facilitate the injection and transportation of holes from the anode 20. Particular hole injection materials are, for example, phthalocyanine, in particular, copper phthalocyanine which is usually used in organic EL devices.

The reference numeral 40 represents a hole transportation layer, which is usually formed with the method similarly as used in the anode 20 by preparing a hole transportation material into a membrane with a thickness of 1 to 100 nm while allowing it to contact with the anode 20.

Particular hole transportation materials are, for example, arylamine, imidazole, oxadiazole, oxazole, triazole, chalcone, styryl anthracene, stilbene, tetraarylethene, triarylamine, triarylethene, triarylmethane, phthalocyanine, fluorenone, hydrazone, N-vinylcarbazole, pyrazoline, pyrazolone, phenylanthracene, phenylenediamine, polyarylalkane, polysilane, and polyphenylenevinylene derivatives; which may be used in an appropriate combination, if necessary.

Chemical compounds, which are large in intramolecular polarization and adhesion property with an anode (ITO, etc.), can be used as hole injecting/transporting substances.

The reference numeral 50 represents a luminescent layer, which is usually formed with the method similarly as used in the anode 20 by preparing one or more coumarin derivatives feasible in the present embodiment and optionally together with a host compound into a single or adjacent separate membrane(s) with a thickness of 10 to 100 nm each while allowing such membranes to contact with the hole transportation layer 40.

As described heretofore, the luminescent layer 50 comprises a green light-emitting coumarin derivative as dopant and hole- and electron-transporting substances as host: Such coumarin derivative contains a plurality of coumarin moieties bound to an aromatic ring, heterocycle or any combination thereof, as well as exhibiting a glass transition point of 150° C. or higher or a melting point of 297° C. or higher.

As to such coumarin derivative, one can employ one or more members chosen from the coumarin derivatives 1, 2 and 3 represented by the following Chemical Formulae 7, 8 and 9 respectively.

Chemical Formula 7:

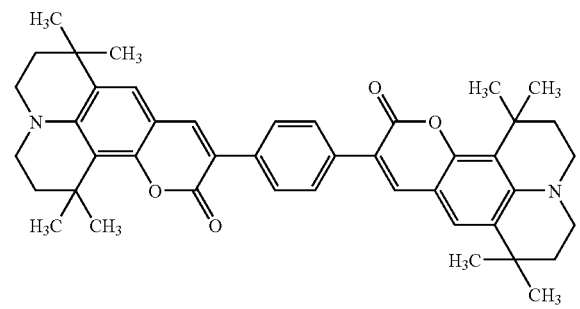

Chemical Formula 8:

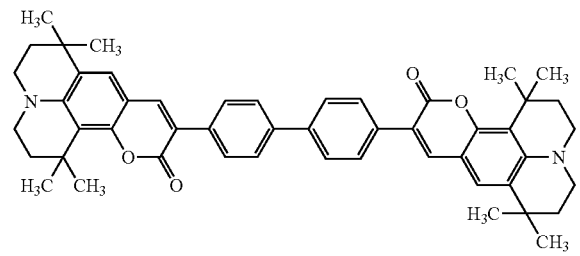

Chemical Formula 9:

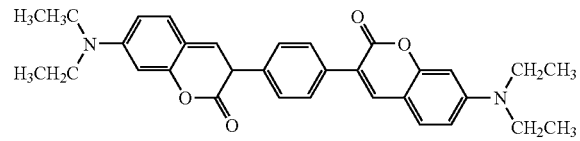

The coumarin derivatives 1 to 3 represented by Chemical Formulae 7 to 9, which exhibit both absorption and luminescence maxima in the visible region and emit a visible light in the bluish green region to the green region when excited, are superior in thermal resistance and useful as luminescent layer material in the organic EL device in this embodiment.

The coumarin derivatives 1 to 3 can be prepared in various ways: With an economical viewpoint, it is preferable to employ a process which utilizes dehydration condensation reaction of aldehyde group with active methylene group.

The coumarin derivatives 1 to 3 is formed in a high yield by allowing p-phenylene diacetonitrile or 4,4'-biphenyldiacetonitrile bearing a phenyl or biphenyl group to react with N,N-diethylminosalicylaldehyde or 1,1,7,7-tetramethyl-8-hydroxy-9formyljulolidine to form a coumarin group.

Prior to use, the coumarin derivatives thus obtained are usually purified with a method(s) usually employed in the purification of analogous compounds, such as dissolution, extraction, separation, decantation, filtration, concentration, thin layer chromatography, column chromatography, gas chromatography, high-performance liquid chromatography, distillation, sublimation, and crystallization; which may be applied in combination, if necessary.

Depending upon the use of the coumarin derivatives, it is desirable to highly purify them with distillation, crystallization and/or sublimation when used in organic EL devices, prior to their use.

Among these methods, sublimation is superior to others because it easily provides high-purity crystals in a single step and a lesser loss of coumarin derivatives, and because it does not substantially incorporate solvents in the resulting crystals.

Although both atmospheric and reduced pressure sublimation methods are applicable to the present invention, the latter is usually employed. To sublimate in vacuo the coumarin derivative in this embodiment, for example, an adequate amount of any of the coumarin derivatives is placed in a sublimation purification apparatus, and then heated at the lowest possible temperature, desirably, at a temperature lower than their melting points while keeping the inner pressure of the apparatus at $10^{-2}$ Torr or lower, desirably, $10^{-3}$ Torr or lower so that the coumarin derivatives are not decomposed.

When the purity of the coumarin derivatives to be subjected to sublimation purification is low, the sublimation rate is reduced so as to avoid the incorporation of impurities by increasing or decreasing the pressure and/or heating temperature in the apparatus, while the sublimation is accelerated by aerating the inner space of the apparatus with an inert gas such as a rare gas when the coumarin derivatives are less sublimable.

The size of crystals obtainable by sublimation can be controlled by elevating or reducing the temperature of the condensation surface in the apparatus: When the condensation surface is kept at a temperature slightly lower than the heating temperature so that the coumarin derivative gradually crystallizes, one can obtain crystals with a larger size.

The following will illustrate synthetic process for the above-mentioned coumarin derivatives 1, 2 and 3 represented by Chemical Formulae 7, 8 and 9 respectively.

Coumarin Derivative 1 Represented by Chemical Formula 7

An adequate amount of xylene was placed in a reaction vessel, suspended with 5.5 g of 1,1,7,7-tetramethyl-8-hydroxy-9-formyljulolidine and 1.56 g of p-phenylenediacetonitrile, added with adequate amounts of acetic acid and pyridine while stirring, dissolved by heating, and reacted for two hours under refluxing conditions.

The reaction mixture was cooled to room temperature, and added with an adequate amount of methanol, after which the resultant crystals were collected and recrystallized by using a mixture of chloroform and methanol, thus obtaining 1.5 g powdery yellow crystal of the coumarin derivative 1 represented by Chemical Formula 7 in this embodiment.

A part of the crystal was sampled, and its visible absorption and fluorescence emission spectra were determined in methylene chloride solution in usual manner, leading to the observation of absorption and fluorescence maxima at wavelengths of around 442 ($\epsilon=7.34\times10^4$) and 508 nm respectively.

The coumarin compound 1 in this embodiment showed a melting point of 369 to 375° C., a glass transition point around 181° C., and a decomposition point around 429° C. when determined by usual differential scanning calorimetry analysis (abbreviated as "DSC analysis" hereinafter).

The $^1$H-NMR spectrum in chloroform deuteride solution was determined in usual manner, revealing peaks at chemical shifts δ (ppm, TMS) of 1.32 (12H, s), 1.60 (12H, s), 1.75 to 1.83 (8H, m), 3.23 to 3.32 (8H, m), 7.26 (2H, s), 7.70 (2H, s), and 7.78 (4H, s).

Coumarin Derivative 2 Represented by Chemical Formula 8

1,1,7,7-Tetramethyl-8-hydroxy-9-formyljulolidine was reacted with 4,4'-biphenyldiacetonitrile similarly as the above mentioned Coumarin derivative 1, obtaining a powdery yellow coumarin derivative 2 represented by Chemical Formula 8 in this embodiment.

A part of the crystal was sampled, and its visible absorption and fluorescence emission spectra in methylene chloride solution were determined in usual manner, leading to the observation of an absorption and a fluorescent maxima at wavelengths of 433 nm ($\epsilon=8.40\times10^4$) and 497 nm, respectively.

The coumarin derivative 2 in this embodiment showed a melting point of 342° C., a glass transition point around 188° C., and a decomposition point around 441° C., when determined by usual DSC analysis.

Coumarin Derivative 3 Represented by Chemical Formula 9

An adequate amount of xylene was placed in a reaction vessel, suspended with 3.86 g of N,N-diethylaminosalicylaldehyde and 1.56 g of p-phenylenediacetonitrile, added with adequate amounts of acetic acid and pyridine while stirring, dissolved by heating, and reacted for two hours under refluxing conditions.

The reaction mixture was cooled to room temperature, and added with an adequate amount of methanol, after which the resultant crystals were collected and recrystallized by using a mixture of chloroform and methanol, thus obtaining 2.0 g powdery yellow crystal of the coumarin derivative 3 represented by Chemical Formula 9 in this embodiment.

A part of the crystal was sampled, and its visible absorption and fluorescence emission spectra were determined in methylene chloride solution in usual manner, leading to the observation of absorption and fluorescence maxima at wavelengths of around 425 nm ($\epsilon=7.68\times10^4$) and 495 nm respectively.

The coumarin derivative 3 in this embodiment showed a melting point of 297 to 310° C., a decomposition point around 419° C., and no glass transition point when determined by usual DSC analysis.

The $^1$H-NMR spectrum in chloroform deuteride solution was determined in usual manner, revealing peaks at chemical shifts δ (ppm, TMS) of 1.23 (12H, t), 3.44 (8H, q), 6.54 (2H, d), 6.60 (2H, dd), 7.33 (2H, d), 7.73 (2H, s), and 7.76 (4H, s).

In the luminescent layer 50, the host is a mixture of a hole transporting substance chosen from materials which function as hole transportation layer 40 as described above, and an electron transporting substance chosen from materials which function as electron transportation layer 60 as described hereinafter.

In this case, the hole transporting substance as host in the luminescent layer 50 is preferably to be the same as that in the hole transportation layer 40. Thus, the injection of holes from the hole transportation layer 40 into the luminescent layer 50 is facilitated to increase the efficiency, and the use of the same substance with different purposes would reduce cost for organic EL devices.

Further, the electron transporting substance as host in the luminescent layer 50 is preferably to be the same as that in the electron transportation layer 60. Thus, the injection of electrons from the electron transportation layer 60 into the luminescent layer 50 is facilitated to increase the efficiency, and the use of the same substance with different purposes would reduce cost for organic EL devices.

The ratio of the hole- and electron transporting substances against hosts in the luminescent layer 50 shall not be restricted to particulars as long as they do not permit emission from host: As to preferred ratios which allow the substances to effectively exhibit the prescribed function when they are in mixture, the hole- and electron-transporting substances are to be in the range of 1 to 90% and 99 to 10% by mass, more desirably, 1 to 10% and 99 to 90% by mass respectively.

This ratio is to retain the balance between holes with a higher mobility and electrons with a lower mobility in the luminescent layer 50 in a prescribed level: If the ratio comes outside the ranges, the mixture host may exhibit no effective function to permit emission in an observable level from the host materials, resulting in a remarkable decay in brightness life expectancy.

The ratio of coumarin derivative as dopant in the luminescent layer 50 against the total amount of host materials can be set to 0.05 to 50% by mass, desirably, 0.1 to 30% by mass.

To enhance durability at elevated temperature, the glass transition points of hole- and electron-transporting substances in the luminescent layer 50 are preferably to be 120° C. or higher.

Now, coming back to in FIG. 1, the reference numeral 60 represents an electron transportation layer, which is usually formed with a method similar to that used in the anode 20 by preparing one or more organic compounds high in electron affinity into a membrane with a thickness of 10 to 100 nm while allowing it to contact with the luminescent layer 50.

In case that a plurality of the electron transportation layer materials are used, they may be mixed to homogeneity and then formed into a single layer, and alternatively formed into a plurality of separate layers without premixing while allowing each layer to contact with its adjacent layer(s).

Preferable electron transporting substances are cyclic ketones or their derivatives such as quinolinol metal complex, benzoquinone, anthraquinone, and fluorine; or silazane derivatives; among which the most preferable material is a quinolinol metal complex.

The wording "quinolinol metal complex(es)" as referred to as in the present invention means complexes in general comprising a quinolinol, such as 8-quinolinol and benzoquino-line-10-ol, which bears a pyridine residue and hydroxyl group intramolecularly and behaves as a ligand; and a univalent, divalent or trivalent metal or its oxide of the group 1, 2, 12 or 13 in the periodic chart of elements, such as lithium, beryllium, magnesium, calcium, zinc, aluminium, gallium and indium, which behaves as a center metal and receives an electron pair from the nitrogen atom in the pyridine residue to form a coordinate bond with the ligand.

In case that ligand is either 8 quinolinol or benzoquinoline-10-ol, it may bear one or more substituents, and never hinders one or more substituents, for example, halogen groups such as fluoro, chioro, bromo, and iodo groups; aliphatic hydrocarbon groups such as methyl, trifluoromethyl, ethyl, propyl, isopropyl, butyl, isobutyl, secbutyl, tert-butyl, pentyl, isopentyl, neopentyl, and tert-pentyl groups; ether groups such as methoxy, trifluoromethoxy, ethoxy, propoxy, isopropoxy, butoxy, isobutoxy, secbutoxy, tert-butoxy, pentyloxy, isopentyloxy, phenoxy, and benzyloxy groups; ester groups such as acetoxy, trifluoroacetoxy, benzoyloxy, methoxyarbonyl, and should be carbonyl suffix; cyano group; nitro group; and suif one group to be bound to carbon(s) other than those at the C-8 or C-10 positions to which hydoxyl group(s) is linked. In case that a quinolinol metal complex has two or more ligands intramolecularly, they may be the same or different each other.

Particular quinolinol metal complexes are, for example, aluminium complexes such as [aluminium-tris(8-quinolinolato), abbreviated as "Alq3" hereinafter], aluminium-tris(3,4-dimethyl-8-quinolinolato), aluminium-tris(4-methyl-8-quinolinolato), aluminium-tris(4-methoxy-8-quinolinolato), aluminium-tris(4,5-dimethyl-8-quinolinolato), aluminium-tris(4,6-dimethyl-8-quinolinolato), aluminium-tris(5-chloro-8-quinolinolato), aluminium-tris-(5-bromo-8-quinolinolato), aluminium-tris(5,7-dichloro-8-quinolinolato), aluminium-tris(5-cyano-8-quinolinolato), aluminium-tris(5-sulfonyl-8-quinolinolato), aluminium-tris(5-propyl-8-quinolinolato), and aluminium-bis(2methyl-8-quinolinolato)oxide.

Particular zinc complexes are, for example, zinc complexes such as zinc-bis(8-quinolinolato), zinc-bis(2-methyl-8-quinolinolato), zinc-bis(2,4-dimethyl-8-quinolinolato), zinc-bis(2-methyl-5-chloro-8-quinolinolato), zinc-bis(2-methyl-5-cyano-8-quinolinolato), zinc-bis(3,4dimethyl-8-quinolinolato), zinc-bis(4,6-dimethyl-8-quinolinolato), zinc-bis(5-chloro-8-quinolinolato), and zinc-bis(5,7-dichloro-8-quinolinolato).

Particular beryllium complexes are, for example, beryllium complexes such as beryllium-bis(8-quinolinolato), beryllium-bis(2-methyl-8-quinolinolato), beryllium-bis(2,4-dimethyl-8-quinolinolato), beryllium-bis(2-methyl-5-chloro-8-quinolinolato), beryllium-bis(2-methyl-5-cyano-8-quinolinolato), beryllium-bis(3,4-dimethyl-8-quinolinolato), beryllium-bis(4,6-dimethyl-8-quinolinolato), beryllium-bis(5-chloro-8-quinolinolato), beryllium-bis(5,7-dichloro-8-quinolinolato), and beryllium-bis(10-hydroxybenzo[h]quinolinolato).

As quinolinol metal complexes other than the above-mentioned complexes, one can choose, for example, magnesium complexes such as magnesium-bis(8-quinolinolato), magnesium-bis(2-methyl-8-quinolinolato), magnesium-bis(2,4-dimethyl-8-quinolinolato), magnesium-bis(2-methyl-5-chloro-8-quinolinolate), magnesium-bis(2methyl-5-cyano-8-quinolinolato), magnesium-bis(3,4-dimethyl-8quinolinolato), magnesium-bis(4,6-dimethyl-8-quinolinolato), magnesiumbis(5-chloro-8-quinolinolato), and magnesium-bis(5,7dichloro-8-quinolinolato); indium complexes such as indium-tris(8-quinolinolato); gallium complexes such as gallium-tris(5-chloro-8-quinolinolato); and calcium complexes such as calcium-bis(5-chloro-8-quinolinolato). The above-mentioned quinolinol metal complexes may be used in combination, if necessary.

The above electron transporting substances are listed only for illustration, and the electron transporting substances feasible in the present invention are intended in no way to limit to these.

In FIG. 1, the reference numeral 70 represents a cathode, which is usually formed by depositing one or more combined metals such as lithium, magnesium, calcium, sodium, lithium, silver, copper, aluminium, indium, and metal oxides and electric conductive compounds with a work function (usually not higher than 5 eV) lower than that for the compound to be used in the electron transportation layer 60 while allowing the resultant layer to come into contact with the electron transportation layer 60.

There is provided no definition for the thickness of the cathode 70: It is set to 10 nm or more thick, desirably, 50-500 nm thick to give a resistivity of 1 kΩ/□ or lower while considering electric conductivity, production cost, thickness of device, and optical transmittance.

To facilitate the transportation of electrons from the cathode 70 to the electron transportation layer 60, there may be provided with a method similar to that used in the anode 20 a membrane of alkaline metal- or alkaline earth metal compound such as lithium fluoride (LiF) or lithium oxide, 0.1 to 2 nm thick, on the side to be contacted with the electron transportation layer 60 in the cathode 70.

Furthermore, there may be provided an interfacial layer of aromatic diamine, quinaqcridone, naphthacene, organic silicon or organic phosphide compounds between the cathode 70 and the electron transportation layer 60 in order to improve their adhesion, if necessary.

As explained heretofore, the organic EL device as a preferred embodiment according to the present invention can be obtained by providing in one device an anode (20), a hole transportation layer (40), a luminescent layer (50), an electron transportation layer (60), a cathode (70) and optionally a hole injection layer (30) on the same substrate while allowing each layer to contact with its adjacent layer(s).

During the formation of each layer, it is desirable to carry out all the working steps under highly vacuumed conditions, particularly, at a pressure of $10^{-5}$ Torr or lower to minimize the oxidation and decomposition of organic compounds, as well as to minimize the adhesion of oxygen and water.

In the formation of the luminescent layer (50), the ratio of host and dopant can be adjusted by premixing them in a prescribed ratio, and alternatively by separately controlling the heating velocities for respective compounds in vacuum sublimation.

To minimize deterioration under operation conditions, it is desirable either to seal a part or whole of the organic EL device thus obtained with a sealing glass or metallic cap in the stream of an inert gas, or to cover it with a protecting membrane such as those of ultraviolet-setting resins.

Now explaining the use of the organic EL device S1 in this embodiment, the organic EL device is driven by intermittently energizing it with a relatively high pulse voltage, or continuously energizing it with a relatively low dc voltage, usually, 3 to 50 V, dependently upon its uses.

The organic EL device S1 gives luminescence only when the anode 20 potential exceeds the cathode 70 potential. Thus, both dc or ac voltages are feasible to energize the organic EL device S1, and the waveform and frequency of such voltages are arbitrary chosen.

When energized with ac, the organic EL device S1 increases or decreases in brightness of luminescence, and repeats on/off for luminescence due to its principle. In case of the organic EL device in FIG. 1, when a voltage is energized between the anode 20 and the cathode 70, holes injected from the anode 20 move into the luminescent layer 50 through the hole injection layer 30 and the hole transportation layer 40, and electrons injected from the cathode 70 move into the luminescent layer 50 through the electron transportation layer 60.

As a result, the holes and electrons recouple each other in the luminescent layer 50 to generate coumarin derivatives in the excited state, and the prescribed green luminescence is released from the coumarin derivatives in the excited state through the anode 20 and the substrate 10.

To suppress the luminescence from host materials in this embodiment, a mixture layer consisting of hole- and electron-transporting substances is used as host material. When such a mixture layer is used, the hole transporting substance transports holes to guest, while the electron transporting substance transports electrons to guest. Thus, the simultaneous injection of holes and electrons into the hole- and electron-transporting substances in host materials is effectively suppressed to reduce any luminescence from host materials, suppressing the decay of host material and enhancing their durability.

Depending upon the type and ratio against host to be used in combination with coumarin derivative, the organic EL device S1 usually has a luminescent maximum, particularly, a fluorescence maximum in the green region, particularly, around 490 to 540 nm.

Further in this embodiment, the molecular weight of coumarin derivative is increased to at least 2-folds larger than those of conventional coumarin derivatives by allowing a plurality of coumarin groups to bind to an aromatic ring, heterocycle or any combination thereof, resulting in significant improvement of coumarin derivatives for heat resistance. (see. Chemical Formulae 7 to 9).

In particular, in this embodiment, the coumarin derivative is designed to exhbit a glass transition point of 150° C. or higher or a melting point of 297° C. or higher. The use of such a coumarin derivative with an enhanced thermal resistance as dopant in the luminescent layer 50 enhances thermal resistance.

Thus, the present invention attains the luminescent layer 50 comprising as dopant a coumarin derivative which is higher in thermal resistance than conventional coumarin derivatives and a host material with an elevated durability, the organic EL device according to the present invention much more improves durability at elevated temperature than conventional organic EL devices.

Further, the organic EL device S1 using coumarin derivative in this embodiment emits a visible light in the green region and the emission consistently prolongs over a long period of time even when driven under high temperature conditions.

As described above, since the organic EL device S1 in this embodiment is superior in durability, high in emission efficiency and in consequence large in brightness, it would have a variety of uses in illuminants and information displaying equipments to visualize information.

Since the illuminants using the organic EL device S1 as light source can be formed into a light panel with a reduced power consumption, they are very useful in light source for general illumination, as well as energy- and space-saving lighting sources, for example, those in liquid crystal devices; copying apparatuses; printing apparatuses; electronic photographic apparatuses; computers and their application apparatuses; controlling instruments directed to industrial uses; electronic measuring apparatuses; analyzing apparatuses; measuring instruments in general; communicating apparatuses; electronic measuring instruments directed to uses in medical treatment; apparatuses to be equipped to cars, automobiles, ships, airplanes, and spaceships; aircraft controlling apparatuses; interiors; signboards; and signs.

In case of applying the organic EL device S1 in this embodiment to information displaying equipments such as computers, televisions, video recorders, computerized game consoles, clocks, telephones, car navigation systems, multimeters for automobile use, oscilloscopes, radars, and sonars, it can be used alone or in combination with blue light- and red light-emitting organic EL devices in full-color displays.

Among these use, the features of the organic EL device S1 in this embodiment can be fully utilized when the organic EL device S1 is applied to displays directed to use in cars and automobiles which require special durability. As to driving modes, usual simple matrix and active matrix mode are applicable.

In case of using the organic EL device S1 in this embodiment in cars and automobiles, it is inevitably exposed to high temperature conditions (for example, around 70 to 80° C.). The organic layers, particularly, that are amorphous undergo crystallization at their glass transition temperatures (Tg) or higher, thus increasing surface irregularity in the layers, and accelerating current leakage. Accordingly, in case of directing to car and automobile uses, the glass transition temperatures (Tg) of all the materials are preferably to be 120° C. or higher.

Further, in case of using the organic EL device S1 in this embodiment in, for example, displays for cars and automobiles, its ambient temperature is around −40° C. to 120° C.

To enhance stability under elevated temperature conditions at such an ambient temperature, it is inevitable to increase the adhesiveness of the hole injection layer 30, particularly, that around the interfacial with the anode 20. This may be due to a significant difference between both layer with respect to their linear expansion coefficients.

Because of this, it is favorable to provide as the hole injection layer 30 adjacent to the anode 20 a layer of porphyrin compound which is less in crystallographic changes.

Particularly, in case of using CuPc as porphyrin compound, preferred CuPcs are those which maintain the variation of diffraction peak accompanied by heating the organic EL device S1 at such an ambient temperature within ±25% of diffraction peak before heating, in terms in values of diffraction peaks as determined by x-ray diffraction analysis of CuPc. The ambient temperature is from −40° C. to 120° C. in this embodiment.

In this case, the diffraction peak of CuPc, which reflects its crystallinity, is from the (200) face of the hole injection layer 30 consisting of CuPc (CuPc membrane 30) located in parallel with the anode 20 when the CuPc membrane 30 is subjected to x-ray diffraction method: It corresponds to the peak appearing at 2θ=6.68° shown in FIG. 2, which will be designated as "CuPc crystallinity peak" hereinafter.

In this embodiment, it is favorable to maintain the variation in CuPc crystallinity peak accompanied by heating the organic EL device S1 at such an ambient temperature within ±25% of CuPc crystallinity peak before heating, in terms of values, in particular, integration values of CuPc crystallinity peak (2θ=6.68°).

The adhesiveness of CuPc membrane can be enhanced by minimizing the variation in CuPc crystallinity peak before and after heating to ±25%. Further, the changes in crystalline state of organic materials can be reduced to a level which causes no short-circuit and electric leakage when used under enhanced temperature conditions.

Figure 2:
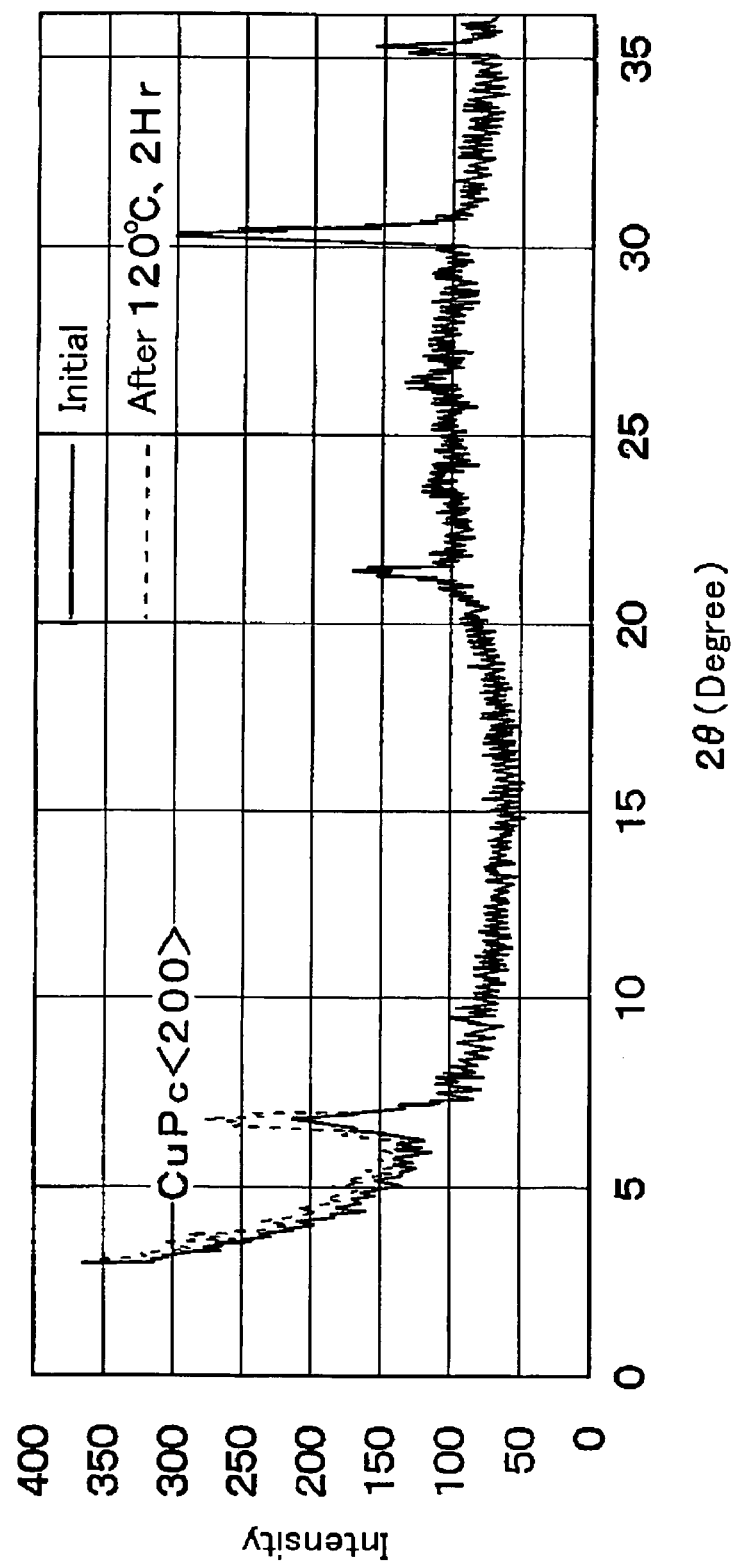
FIG. 2 is to show the results of x-ray diffraction analysis on CuPc membrane for crystallinity carried out before and after accelerating high temperature standing.

In the data shown in FIG. 2, the value of CuPc crystallinity peak after heating significantly changed (1.5-fold larger than that before heating), which would accelerate short-circuit and electric leakage. Such a CuPc membrane 30, where the variation in CuPc crystallinity peak before and after heating is suppressed to ±25%, is attainable by, for example, first subjecting the surface of the anode 20 as base to ultraviolet ozone treatment at 150° C., then depositing CuPc on the anode 20 at a material-heating temperature of 520° C. into a membrane.

In this embodiment, by preparing the CuPc membrane 30 in this manner, one can enhance the adhesiveness of the hole injection layer 30 and provide the organic EL device S1 which would endure much higher temperature conditions.

As mentioned above, it is important to impart a property of less changing crystallinity in the hole injection layer 30 under elevated temperature conditions upon formation of devices. Because of this, in FIG. 1, the surface roughness of the anode 20 becomes one of important factors which permit a crystalline material to form a stabilized membrane having a high crystallinity on the anode 20. In other words, a more smooth surface gives a membrane which is more stable and more crystalline.

In case of using ITO as the anode 20 in this embodiment, its mean height of surface roughness profile (Ra) is preferably to be 2 nm or less, while the ten point mean height of surface roughness profile (Rz) is to be 20 nm or less. In the embodiment of FIG. 1, for example, the surface of ITO as the anode 20 formed on the glass substrate 10 can be ground to give an Ra of about 1 nm or lower or an Rz of about 10 nm.

The preferred embodiments according to the present invention will be illustrated with references to the following Examples which are intended in no way to limit the scope of the present invention, as well as to Comparative Examples.

EXAMPLE 1

The anode 20 of ITO, thickness of 150 nm, is formed on the substrate 10 of glass by the spattering method. After patterning, the surface of ITO is smoothed by grinding: The mean height of surface roughness profile (Ra) of ITO is preferably to be 2 nm or less, while its ten point mean height of surface roughness profile (Rz) is to be 20 nm or less. This example uses an ITO where the surface has been ground to an Ra of about 1 nm or less and an Rz of about 10 nm.

On the anode 20 is formed the hole injection layer 30 of copper phthalocyanine, thickness of 15 nm, by the vacuum vapor deposition method. Further, the hole transportation layer 40 of triphenylamine tetramer represented by Chemical Formula 10, thickness of 40 nm, is formed by the vacuum vapor deposition method.

Chemical Formula 10:

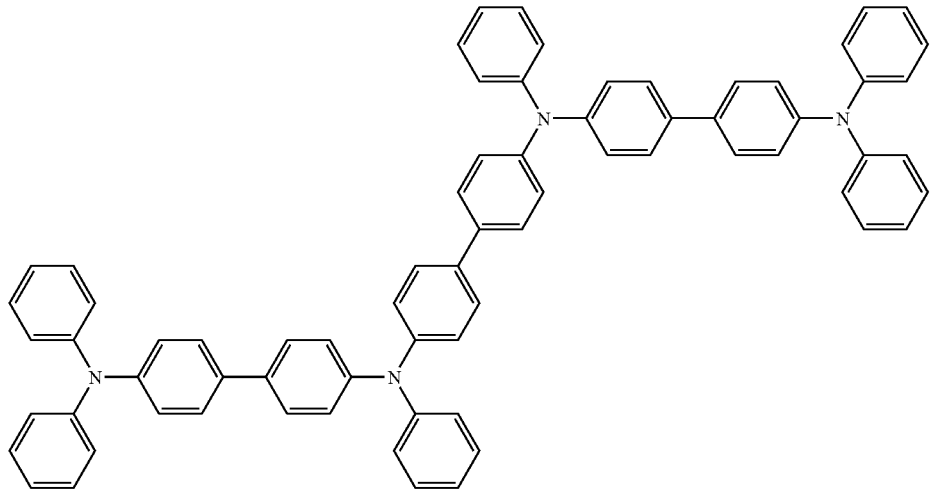

Thereafter, formed is the luminescent layer 50, thickness of 40 nm, which consists of 2% by mass of the coumarin derivative 1 represented by the above Chemical Formula 7 as dopant, 49% by mass of aluminum chelate (Alq3) as host material, and 49% by mass of triphenylamine tetramer. Further, Alq3 is deposited to form the electron transportation layer 60, thickness of 20 nm.

After forming these organic layers, LiF was formed into a membrane as cathode 70, thickness of 0.5 nm, and Al was formed thereon into a membrane, thickness of 100 nm, thus obtaining an organic EL device as green light-emitting device. The chromaticity was (0.28, 0.62) on the chromaticity diagram established by International Commission on Illumination (CIE).

The brightness half life was 1,200 hours when the device was continuously allowed to emit luminescence at 85° C. and 400 Cd/m$^2$ in 1/64 duty driving mode. As described above, this Example attained an organic EL device which had an enhanced durability at elevated temperature and consistently emitted a visible light in the green region over a long period of time even when driven under elevated temperature conditions.

EXAMPLE 2

A green light-emitting device was obtained similarly as in Example 1, except that it used the luminescent layer 50, thickness of 40 nm, which consists of 2% by mass of the coumarin derivative 1 represented by the Chemical Formula 7 as dopant, 94% by mass of Alq3 as host material, and 4% by mass of triphenylamine tetramer. The chromaticity was (0.28, 0.62) on the chromaticity diagram established by CIE.

The brightness half life was 1,500 hours when the device was continuously allowed to emit luminescence at 85° C. and 400 Cd/m$^2$ in 1/64 duty driving mode. As described above, this Example attained an organic EL device which had an enhanced durability at elevated temperature and consistently emitted a visible light in the green region over a long period of time even when driven under elevated temperature conditions.

Further, in this Example an organic EL device superior in durability to that in Example 1 was attained because the mixing ratio against host in the luminescent layer 50 was optimized.

COMPARATIVE EXAMPLE 1

A green luminescent device was obtained similarly as in Example 1 except that it used the luminescent layer 50, thickness of 40 nm, which consists of only 2% by mass of the coumarin derivative 1 represented by the Chemical Formula 7 as dopant and 98% by mass of Alq3 as host material. The chromaticity was (0.28, 0.62) on the chromaticity diagram established by CIE.

The brightness half life was 500 hours when the device was continuously allowed to emit luminescence at 85° C. and 400 Cd/m$^2$ in 1/64 duty driving mode.

EXAMPLE 3

A green light-emitting device was obtained similarly as in Example 1 except that it used the luminescent layer 50, thickness of 40 nm, which consists of 1% by mass of the coumarin derivative 2 represented by the Chemical Formula 8 as dopant, 74% by mass of Alq3 as host material, and 25% by mass of triphenylamine tetramer. The chromaticity was (0.27, 0.60) on the chromaticity diagram established by CIE.

The brightness half life was 1,000 hours when the device was continuously allowed to emit luminescence at 85° C. and 400 Cd/m$^2$ in 1/64 duty driving mode. As described above, this Example attained an organic EL device which had an enhanced durability at elevated temperature and consistently emitted a visible light in the green region over a long period of time even when driven under elevated temperature conditions.

COMPARATIVE EXAMPLE 2

A green light-emitting device was obtained similarly as in Example 1 except that it used the luminescent layer 50, thickness of 40 nm, which consists of 2% by mass of COUMARIN 6, a typical conventional coumarin material, represented by the Chemical Formula 11 as dopant, 49% by mass of Alq3 as host material, and 49% by mass of triphenylamine tetramer. The chromaticity was (0.28, 0.62) on the chromaticity diagram established by CIE.

Chemical Formula 11:

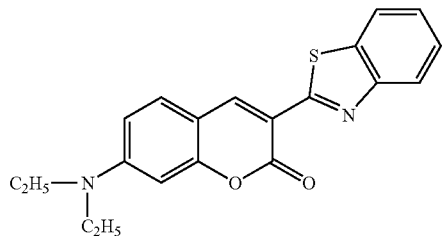

The brightness half life was 400 hours when the device was continuously allowed to emit luminescence at 85° C. and 400 Cd/m² in 1/64 duty driving mode.

COMPARATIVE EXAMPLE 3

A green light-emitting device was obtained similarly as in Example 1 except that it used the luminescent layer 50, thickness of 40 nm, which consists of only 2% by mass of COUMARIN 6 as dopant and 98% by mass of Alq3 as host material. The chromaticity was (0.28, 0.62) on the chromaticity diagram established by CIE.

The brightness half life was 300 hours when the device was continuously allowed to emit luminescence at 85° C. and 400 Cd/m² in 1/64 duty driving mode.

EXAMPLE 4

A green light-emitting device was obtained similarly as in Example 1 except that it used the luminescent layer 50, thickness of 40 nm, which consists of 2% by mass of the coumarin derivative 3 represented by the Chemical Formula 9 as dopant, 49% by mass of aluminum-tris(3,4-dimethyl-8-quinolinolato) as host material, and 49% by mass of N,N'-bis{4-diphenylamino-4'-biphenyl}-N,N'-diphenyl-9,9'-bis(4-aminophenyl)fluorene. The chromaticity was (0.27, 0.60) on the chromaticity diagram established by CIE.

The brightness half life was 1,000 hours when the device was continuously allowed to emit luminescence at 85° C. and 400 Cd/m² in 1/64 duty driving mode. As described above, this Example attained an organic EL device which had an enhanced durability at elevated temperature and consistently emitted a visible light in the green region over a long period of time even when driven under elevated temperature conditions.

INDUSTRIAL APPLICABILITY

As explained heretofore, the present invention is based on the discovery of a remarkable enhancement in durability at elevated temperature in organic EL devices using coumarin derivatives as dopant. The thermal resistance of the coumarin derivative usable in the present invention is significantly improved by allowing it to bear a molecular weight at least 2-fold larger than those in conventional coumarin derivatives, and as a result the use of such coumarin derivative as dopant in the luminescent layer enhances durability at elevated temperature in the organic EL devices. Further, the durability at elevated temperature can be much more enhanced by using as host in luminescent layer a mixture of a material which functions as hole transportation layer, and another material which functions as electron transportation layer. Because of these, the organic EL devices are extremely useful in illuminants in general and also in a variety of information displaying equipments to visualize information, for example, those of images and words.

The present invention, which attains such outstanding effects, would be a significant invention that greatly contributes to this art.

The invention claimed is:

1. An organic electroluminescent device bearing an anode, a hole injection layer, a hole transportation layer, a luminescent layer, an electron transportation layer and a cathode, characterized in that (i) all the materials used in said hole injection layer, said hole transportation layer, said luminescent layer, and said electron transportation layer have a glass transition temperature (Tg) of 120° or higher, and (ii) said luminescent layer comprises a green light-emitting coumarin derivative as dopant and hole-transporting and electron-transporting substances as host; (iii) said coumarin derivative comprising a plurality of coumarin groups bond to an aromatic ring, heterocycle or any combination thereof, and exhibiting a glass transition point of 150° C. or higher or a melting point of 297° C. or higher, and that (iv) said hole injection layer consisting of a copper phthalocyanine is provided between said anode and said hole transportation layer, and (v) the variation in diffraction peak accompanied by heating said organic EL device at ambient temperature in the range of –40 to 120° C. is maintained within ±25% of the diffraction peak before the heating, in terms of values of diffraction peaks as determined by applying x-ray diffraction method to said copper phthalocyanine, wherein said coumarin derivative is a member selected from the group consisting of:

Chemical Formula 1:

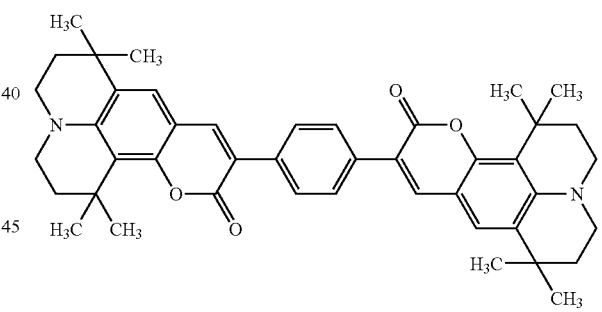

Chemical Formula 2:

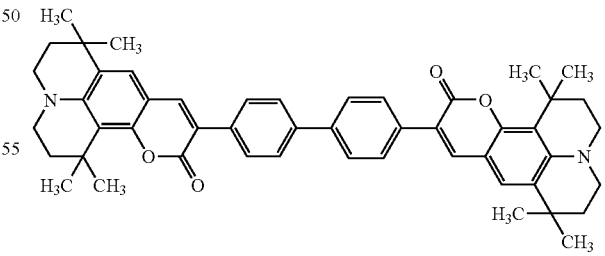

Chemical Formula 3:

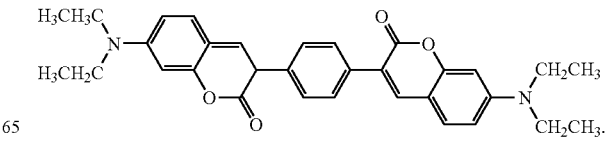

2. The organic electroluminescent device of claim 1, characterized in that said hole transporting substance in said luminescent layer is the same as that in said hole transportation layer.

3. The organic electro-luminescent device of claim 1, characterized in that said electron transporting substance in the luminescent layer is the same as that in said electron transportation layer.

4. The organic electro-luminescent device of claim 1, characterized in that said hole transporting substance in said luminescent layer is the same as that in said hole transportation layer, as well as in that said electron transporting substance in said luminescent layer is the same as that in said electron transportation layer.

* * * * *